Figure 1:
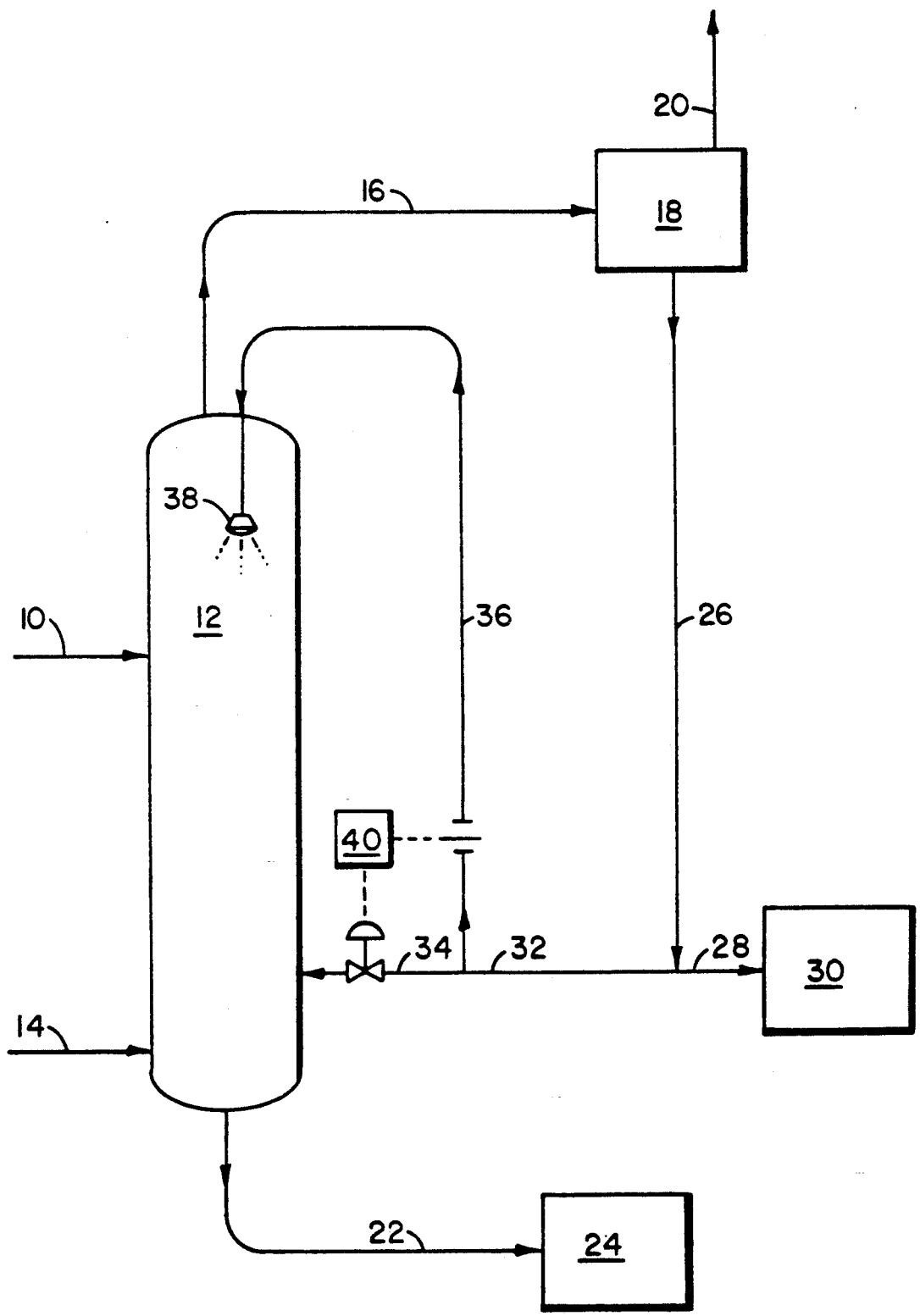

A United States Patent [19]

Tennant et al.

[11] Patent Number: 5,087,741
[45] Date of Patent: Feb. 11, 1992

[54] CONTINUOUS PRODUCTION OF AROMATIC CARBOXYLIC ACIDS

[75] Inventors: Brent A. Tennant; Terry D. Bryson, both of Kingsport, Tenn.

[73] Assignee: Eastman Kodak Company, Rochester, N.Y.

[21] Appl. No.: 619,568

[22] Filed: Nov. 29, 1990

[51] Int. Cl.⁵ .......................................... C07C 51/265
[52] U.S. Cl. .................................... 562/414; 562/413; 562/416
[58] Field of Search ........................ 562/413, 414, 416

[56] References Cited
U.S. PATENT DOCUMENTS
4,777,287 10/1988 Zeitlin et al. ........................ 562/414

Primary Examiner—Jose G. Dees
Assistant Examiner—Vera C. Clarke
Attorney, Agent, or Firm—J. Frederick Thomsen; William P. Heath, Jr.

[57] ABSTRACT

Disclosed is an improved process for the continuous production of aromatic carboxylic acids such as terephthalic acid by the liquid-phase oxidation of an alkyl aromatic compound using an oxygen-containing gas. Operation of the process is improved by providing a spray of recycled reaction medium at or near the top of a columnar oxidation vessel to minimize entrainment of liquid and/or solid components of the reactor in the process off-gas.

3 Claims, 1 Drawing Sheet

CONTINUOUS PRODUCTION OF AROMATIC CARBOXYLIC ACIDS

This invention pertains to an improved method for the continuous production of aromatic carboxylic acids by the liquid-phase oxidation of alkyl aromatic compounds with molecular oxygen in the presence of an oxidation catalyst or catalyst system. More particularly, this invention pertains to such oxidation processes carried out in a columnar reactor provided with means to inhibit entrainment of liquid and/or solid components of the reactor in the process off-gas.

The liquid-phase oxidation of an alkyl aromatic compound to an aromatic carboxylic acid is a highly exothermic reaction commonly carried out in a vented, intimately-mixed, columnar reaction vessel. The oxidation process comprises continuously feeding separately or in admixture an alkyl aromatic compound, fresh and/or recycled solvent and catalyst components to the reaction vessel to which a molecular oxygen-containing gas also is fed, normally at or near the bottom of the vessel. The aromatic carboxylic acid product is sparingly soluble in the process solvent and is removed continuously through a lower exit port located at or near the base of the reactor as a slurry in the solvent which also contains soluble catalyst components. After separation of the aromatic carboxylic acid product, the solvent is returned to the reaction vessel.

The oxygen-depleted process gas, e.g., containing up to about 9 volume percent oxygen, along with minor amounts of solvent decomposition products, is removed through an upper exit port located at or near the top of the reaction vessel. The heat of reaction is removed by the vaporization of the process solvent through the upper exit port. The solvent is condensed from the reactor off-gas by means of one or more condensers. A portion of the condensed solvent is subjected to a water removal step to remove a portion of the water of reaction from the production system and the water-depleted solvent is recycled to the reactor. The other portion of the condensed material is returned directly to the reaction vessel.

The molecular oxygen-containing gas is continuously fed at or near the base of the columnar reaction vessel. The process gas rises through the liquid contents of the reactor resulting in vigorous agitation of the reaction mixture and providing intimate contact between the alkyl aromatic compound and the process solvent having dissolved therein the catalyst or catalyst components.

The described production system can be utilized in the manufacture of aromatic carboxylic acids at excellent production rates relative to the volume of the reaction vessel. One problem that is presented by the production system is the entrainment of solids, including solids dissolved in entrained process solvent, and unreacted aromatic compounds in the off-gas which is removed at or near the top of the reactor. The lines through which the off-gas is transported can be blocked or plugged by the deposition of the entrained solids therein. The entrained solids also can foul or even plug the condensers fed by the lines and the equipment used in the removal of some of the water from the condensate. To avoid fouling or plugging of the referenced processing equipment by entrained solids, a relatively large space must be maintained above the vigorously frothing or foaming gas/liquid reaction mixture, i.e., the space between the surface of the gas/liquid mixture and the upper exit port. It is apparent that the maintenance of such a large space necessarily limits the utilization and production rate of the reaction vessel.

The present invention provides a means for overcoming the above-described problem while permitting the use of higher levels of the gas/liquid reaction medium within the reactor. These and other advantages are afforded by carrying out the oxidation of an alkyl aromatic compound in a columnar reaction vessel by spraying a reflux mixture of the process solvent, i.e., the condensed solvent vaporized to remove heat from the reaction vessel, from one or more spray nozzles located between the upper exit port and the gas/liquid reaction mixture. When the exit port is in the head of the reactor and the spray means are located at nearly the same elevation, e.g., within 70 cm of the exit port, up to about 95% of the volume of the reactor may be filled with reaction mixture. Our invention also decreases the amounts of bromine and bromine-containing compounds in the off-gas which decreases significantly the rate of corrosion of the piping, condensers and water removal equipment, and apparatus used in the transport and processing of the off-gas. Another advantage provided by the process described herein is a significant reduction in the amount of aqueous, aliphatic acid solvent which needs to be processed in the water removal system.

Our invention thus provides a method for the continuous production of an aromatic carboxylic acid in a pressurized oxidation reactor by liquid-phase, exothermic oxidation of an alkyl aromatic compound with an oxygen-containing gas in the presence of an oxidation catalyst and aqueous, $C_2$ to $C_6$ aliphatic, monocarboxylic acid reaction medium which comprises the steps of:

(1) continuously feeding to the reactor the alkyl aromatic compound, the aqueous, monocarboxylic acid reaction medium having the oxidation catalyst dissolved therein and an oxygen-containing gas;

(2) continuously removing from the lower portion of the reactor an oxidizer product comprising the aromatic carboxylic acid and the aqueous, monocarboxylic acid reaction medium having the oxidation catalyst dissolved therein;

(3) continuously removing from the upper portion of the reactor oxygen-depleted gas and vaporized aqueous, monocarboxylic acid reaction medium;

(4) condensing from the stream of step (3) the aqueous, monocarboxylic acid reaction medium; and (5) returning at least a portion of the condensed, aqueous, monocarboxylic acid reaction medium obtained in step (4) in the form of a spray between the top of the gas/liquid contents of the reactor and the point within the reactor which the stream of step (3) is removed.

The accompanying FIGURE is a process flow diagram illustrating a system embodying the principles of the method of the present invention.

While the present invention is susceptible to embodiment in various forms, there is shown in the accompanying FIGURE and hereinafter described in detail a preferred embodiment of the invention. The present disclosure is to be considered as an exemplification of the invention without limitation to the specific embodiment illustrated, however.

Referring to the accompanying FIGURE, reactor feed mixture is introduced via conduit 10 into oxidation reactor 12. The reactor feed mixture comprises an alkyl aromatic compound, an aqueous, $C_2$ to $C_6$ monocarboxylic aliphatic acid solvent, and a suitable oxidation catalyst. The aliphatic, carboxylic acid solvent feed typically contains up to about 15 weight percent water. The feed mixture may further include a suitable promoter. If desired, the alkyl aromatic compound, and/or aliphatic acid solvent containing catalyst components may be fed to reactor 12 at a plurality of points along the side of the reactor. An oxygen-containing gas under pressure is introduced via conduit 14 to reactor 12. The preferred oxygen-containing gas is air. The flow rate of the oxygen-containing gas to reactor 12 is controlled to maintain between 2 and 9 volume percent oxygen (calculated on a dry, solvent free basis) in the off-gas which exits the reactor via conduit 16. The reactants in reactor 12 are maintained at an elevated pressure sufficient to maintain the contained, volatilizable reaction medium substantially in the liquid state at the reaction temperature.

Reactor 12 is a columnar, pressurized, oxidation reactor vessel wherein liquid-phase exothermic oxidation of the alkyl aromatic compound by the oxygen-containing gas takes place in the presence of the oxidation catalyst. The reaction medium contained by reactor 12 thus comprises the oxygen-containing gas, the aromatic alkyl that is to be oxidized to an aromatic carboxylic acid product, the catalyst, and the aqueous, $C_2$ to $C_6$ monocarboxylic aliphatic acid solvent. The amount of water present normally does not exceed about 15 weight percent based on the weight of the water and the aliphatic, carboxylic acid. Typically, the generally-cylindrical, oxidation vessel has a height:diameter ratio in the range of about 8 to 40.

During the course of the oxidation reaction, exothermic heat of reaction, generated by the oxidation of the alkyl aromatic compound, is removed from reactor 12 by vaporization of a portion of the liquid reaction medium. These vapors, along with the oxygen-depleted process gas containing minor amount of decomposition products and bromine-containing compounds, pass upwardly through reactor 12 and are introduced via conduit 16 into a condenser system 18 comprising one or more condensers and a reflux tank. The condensible components of the vapors collected in condenser system 18 consist primarily of the aqueous, aliphatic acid solvent which is returned to reactor 12 as described in more detail hereinbelow. The non-condensible components are vented from the production system via conduit 20.

In operation, reactor 12 continuously produces an aromatic carboxylic acid product that is continuously withdrawn as a slurry in the aqueous, aliphatic acid process solvent, which also contains dissolved catalyst, from the bottom portion of reactor 12 and conveyed via conduit 22 to a suitable solid/liquid separation system 24. The liquid phase recovered from separation system 24 is combined with fresh alkyl aromatic compound and recycled to reactor 12.

A portion of the condensed liquids collected in condenser system 18 is conveyed by means of conduits 26 and 28 to water removal system 30 wherein a substantial portion of the water of the aqueous, aliphatic acid solvent collected in condenser system 18 is removed from the process. The dehydrated process solvent produced in water removal system 30 is recycled to reactor 12.

A second portion of the condensate collected in condenser system 18 is recycled via conduits 26, 32, 34 and 36 directly to reactor 12. In accordance with our invention, all or a portion of the directly recycled condensate is fed to reactor 12 by means of spray head 38 located below exit conduit 16. The amount of directly recycled condensate returned to reactor 12 via lines 26, 32 and 36 through spray head 38 is controlled by flow controller 40 and is between about 10 and 100%. Spray means 38 is designed to distribute the recycled condensate in a finely divided form. e.g., droplets, over a substantial portion, preferably over all, of the surface of the gas/liquid reaction mixture contained within the reactor. The particular means employed to return condensate in the form of a spray to the reactor is not critical to the operation of our invention so long as it provides liquid-gas contact at the top of the reactor. Thus, the condensate spray may be created by means of a single spray head as shown in the FIGURE or by a plurality of spray nozzles.

The spray of recycled condensate provides a plurality of advantageous effects. It knocks down entrained solids and vaporized material which produce solids upon cooling, thereby preventing the fouling or plugging of process equipment such as lines, condensers and distillation columns. The spray permits the presence of higher concentrations of water in the direct recycle stream since a substantial portion of the water content of the spray is vaporized and removed from the reactor, i.e., the higher water concentration does not cause an increase in the water content of the gas/liquid reaction mixture. As a result, the total amount of aqueous, aliphatic acid solvent fed to water removal system 30 is reduced and the operating efficiency of the water removal system is increased. It also decreases the concentration of bromine-containing compounds in vapor line 16 which decreases the rate of corrosion of process equipment. The spray also permits the use of higher pressures and higher levels of the gas/liquid reaction mixture within the reactor which increase the overall efficiency of the process.

Suitable alkyl aromatic compounds useful as reactor feed-mixture components or ingredients in the method of the present invention include mono-, di- and tri-alkyl benzenes and naphthalenes such as toluene, o-xylene, m-xylene, p-xylene, the triethylbenzenes, 2,6-dimethylnaphthalene, 2,7-dimethylnaphthalene and 2,6-diisopropylnapthalene. The respective aromatic carboxylic acid products of these alkyl aromatic compounds are benzoic acid, orthophthalic acid, isophthalic acid, terephthalic acid (TPA), the benzenetricarboxylic acids and 2,6- and 2,7-naphthalenedicarboxylic acids. The method of the invention can be used to produce TPA, isophthalic acid, and trimellitic acid (1,2,4-benzene tricarboxylic acid). It is particularly well suited for the production of benzenedicarboxylic and naphthalenedicarboxylic acids, especially TPA.

Suitable aqueous aliphatic acid solvents useful in the method of this invention are those that are readily volatilizable at the reaction temperatures. Among such solvents are aqueous solutions of $C_2$ to $C_6$ monocarboxylic acids, e.g., acetic acid, propionic acid, n-butyric acid, isobutyric acid, n-valeric acid, trimethylacetic acid, caprioic acid, and mixtures thereof. Preferably, the volatilizable monocarboxylic aliphatic acid solvent is an aqueous acetic acid solution.

The catalyst systems which may be employed in the oxidation process include any catalyst system conventionally used for liquid-phase oxidation of an alkyl aromatic compound. A suitable catalyst system may include a mixture of cobalt, manganese and bromine compounds or complexes, soluble in the particular volatilizable aqueous solvent employed.

As an example, as p-xylene is oxidized to produce TPA practicing the method of the present invention, the usual process conditions and parameters can be summarized as follows: The contents of reactor 12 are subjected to a pressure in the range of about 3.8 to about 7.9 bar absolute (about 55 to 115 psia) at a temperature in the range of about 120° to 180° C.

The following example describes the operation of the production system described in the FIGURE to produce 1000 parts by weight of TPA per day. The amounts of materials are given in parts by weight.

Aqueous acetic acid containing dissolved catalyst was fed at the rate of 3.1 parts per minute and p-xylene was fed at the rate of 0.45 parts per minute via conduit 10 to reactor 12 which consisted of a cylindrical pressure vessel having a height:diameter ratio of 13.3. Air was fed via conduit 14 at a rate of 2.0 parts per minute. The gas/liquid oxidation reaction mixture filled approximately 85% of the volume of the reactor. The temperature of the vigorously mixed reaction mixture was 155° C. and the pressure was controlled at 5.42 bar absolute (64 psig). Oxidizer product consisting of a slurry of 30 weight percent TPA in aqueous acetic acid containing dissolved catalyst was removed from the base of the reactor via line 22 at the rate of 2.4 parts per minute. A vapor stream comprising oxygen-depleted air, acetic acid and water was removed continuously via a port located at the top of the sidewall of the reactor and transported via conduit 16 to condenser system 18 wherein 6.6 parts per minute of condensate consisting essentially of acetic acid and water was collected. A portion of the condensate was fed via conduits 26 and 28 to water removal system 30. The remainder of the condensate was recycled directly to the reactor via conduits 26, 32, 34 and 36 and spray head 38 at the rate of 4.6 parts per minute.

Continuous operation of the process as described results in a decrease in the amounts of solids deposited in off-gas line 16 and in the condensers of condenser system 18. The concentration of bromine-containing compounds in the vapor take-off and recycled condensate was 48 parts per million by weight.

The above-described reactor was used to oxidize p-xylene to TPA without the use of the condensate recycle via the spray head. Thus, aqueous acetic acid containing dissolved catalyst was fed at the rate of 3.1 parts per minute and p-xylene was fed at the rate of 0.45 parts per minute via conduit 10 to reactor 12. Air was fed via conduit 14 at a rate of 2.0 parts per minute. The gas/liquid oxidation reaction mixture filled approximately 57% to 76% of the volume of the reactor. The temperature of the reactor was 155° C. and the pressure was controlled at 5.42 bar absolute (64 psig). Oxidizer product consisting of a slurry of 30 weight percent TPA in aqueous acetic acid containing dissolved catalyst was removed from the base of the reactor via line 22 at the rate of 2.4 parts per minute. A vapor stream comprising oxygen-depleted air, acetic acid and water was removed continuously as described previously and transported via conduit 16 to condenser system 18 wherein 6.6 parts per minute of condensate consisting essentially of acetic acid and water was collected. A portion of the condensate was fed via conduits 26 and 28 to water removal system 30 at a rate of 3.2 parts per minute. The remainder of the condensate was recycled directly to the reactor via conduits 26, 32 and 34 at the rate of 3.4 parts per minute. Conduit 36 and spray head 38 were not used.

Operation of the process without the use of a spray of condensate over the gas/liquid reaction mixture resulted in the deposition of significantly more solids in off-gas line 16 and the condensers of condenser system 18. The deposition of solids can cause severe fouling and plugging of such equipment upon extended operation of the production system, thereby requiring more frequent shutdowns for maintenance and/or replacement of equipment. Operation without the spray resulted in a concentration of bromine compounds of 97 parts per million by weight in the vapor take-off and recycled condensate.

The invention has been described in detail with particular reference to preferred embodiments thereof, but it will be understood that variations and modifications can be effected within the spirit and scope of the invention.

We claim:

1. Method for the continuous production of an aromatic carboxylic acid in a pressurized oxidation reactor by liquid-phase, exothermic oxidation of an alkyl aromatic compound with an oxygen-containing gas in the presence of an oxidation catalyst and aqueous $C_2$ to $C_6$ aliphatic, monocarboxylic acid reaction medium which comprises the steps of:
   (1) continuously feeding to the reactor the alkyl aromatic compound, the aqueous, monocarboxylic acid reaction medium having the oxidation catalyst dissolved therein and an oxygen-containing gas;
   (2) continuously removing from the lower portion of the reactor an oxidizer product comprising the aromatic carboxylic acid and the aqueous, monocarboxylic acid reaction medium having the oxidation catalyst dissolved therein;
   (3) continuously removing from the upper portion of the reactor oxygen-depleted gas and vaporized aqueous, monocarboxylic acid reaction medium;
   (4) condensing from the stream of step (3) the aqueous, monocarboxylic acid reaction medium; and
   (5) returning at least a portion of the condensed, aqueous, monocarboxylic acid reaction medium obtained in step (4) in the form of a spray between the top of the gas/liquid contents of the reactor and the point within the reactor which the stream of (3) is removed.

2. Method according to claim 1 wherein the aromatic carboxylic is a benzene dicarboxylic acid, the alkyl aromatic compound is xylene and the monocarboxylic acid is acetic acid.

3. Method for the continuous production of terephthalic acid in a pressurized oxidation reactor by liquid-phase, exothermic oxidation of p-xylene with an oxygen-containing gas in the presence of an oxidation catalyst and aqueous acetic acid reaction medium which comprises the steps of:
   (1) continuously feeding to the reactor p-xylene, aqueous, acetic acid reaction medium having the oxidation catalyst dissolved therein and an oxygen-containing gas;
   (2) continuously removing from the lower portion of the reactor an oxidizer product comprising terephthalic acid and aqueous acetic acid reaction medium having the oxidation catalyst dissolved therein;

(3) continuously removing from the upper portion of the reactor oxygen-depleted gas and vaporized aqueous, acetic acid reaction medium;
(4) condensing from the stream (3) aqueous, acetic acid reaction medium; and
(5) returning 10 to 100% of the condensed, aqueous, acetic acid reaction medium obtained in step (4) in the form of a spray between the top of the gas/liquid contents of the reactor and the point within the reactor which the stream of step (3) is removed.

* * * * *